(12) United States Patent
D'Orchymont et al.

(10) Patent No.: US 7,842,711 B2
(45) Date of Patent: Nov. 30, 2010

(54) INDAZOLECARBOXAMIDE DERIVATIVES FOR THE TREATMENT AND PREVENTION OF MALARIA

(75) Inventors: Hugues D'Orchymont, Strasbourg (FR); Laurent Fraisse, Balma (FR); André Zimmermann, Achenheim (FR)

(73) Assignee: Sanofi-Aventis, Paris (FR)

( * ) Notice: Subject to any disclaimer, the term of this patent is extended or adjusted under 35 U.S.C. 154(b) by 972 days.

(21) Appl. No.: 11/531,332

(22) Filed: Sep. 13, 2006

(65) Prior Publication Data

US 2007/0185187 A1    Aug. 9, 2007

Related U.S. Application Data

(63) Continuation of application No. PCT/FR2005/000612, filed on Mar. 15, 2005.

(30) Foreign Application Priority Data

Mar. 16, 2004   (FR) ................... 04 02702

(51) Int. Cl.
  *A01N 43/56* (2006.01)
  *A61K 31/47* (2006.01)
  *A61K 31/44* (2006.01)
  *A61K 31/505* (2006.01)
  *A61K 31/425* (2006.01)
  *A61K 31/41* (2006.01)

(52) U.S. Cl. ............... 514/403; 514/307; 514/300; 514/332; 514/333; 514/275; 514/381; 514/365

(58) Field of Classification Search ............ 514/403, 514/307, 300, 332, 333, 275, 381, 365
See application file for complete search history.

(56) References Cited

U.S. PATENT DOCUMENTS 3,457,269 A   7/1969   Kirchner

2006/0004000 A1   1/2006   D'Orchymont et al.

FOREIGN PATENT DOCUMENTS

| EP | 0 410 509 A1 | 1/1991 |
|---|---|---|
| WO | WO 94/05642 | 3/1994 |
| WO | WO 01/72745 | * 10/2001 |
| WO | WO 01/85726 A1 | 11/2001 |
| WO | WO 2004/014864 | 2/2004 |
| WO | WO 2004/014922 A1 | 2/2004 |
| WO | WO2004/031158 | 4/2004 |

OTHER PUBLICATIONS

Fischer, et al., Functions and Pharmacological Inhibitors of Cyclin-dependent Kinases, Celltransmissions—Newsletter for Cell Signaling and Neuroscience Research, V.19, No. 1, Mar. 2003, pp. 1-9.
Knockaert, et al., Pharmacological Inhibitors of Cyclin-dependent Kinases, Trends in Pharmacological Sciences, V.23, No. 9, Sep. 2002, pp. 417-425.
Desjardins et al, Quantitative Assessment of Antimalarial Activity In Vitro by a Semiautomated Microdilution Technique, Antimicrobial Agents and Chemotherapy, Dec. 1979, vol. 16, No. 6, pp. 710-718.
E. Hannig et al, Zur Darstellung einiger Derivate der 5-Methylindazole-3-carbonsaure, Pharmazie, Veb Vertag Volk und Gesundheit, Berlin, DD, vol. 28, No. H 11/12, 1973, pp. 720-721.
Hannig et al, English Language Abstract of Pharmazie (1973), 28(11-12), 720-3, Chem. Abstract.
Waters et al, Cyclin-Dependent protein Kinases as Therapeutic drug Targets for antimalarial Drug Development, Expert Opin. Ther. Targets (2003) vol. 7, No. 1, pp. 7-17.

* cited by examiner

*Primary Examiner*—Shengjun Wang
(74) *Attorney, Agent, or Firm*—Ronald G. Ort

(57) ABSTRACT

The invention relates to methods of treating or preventing malaria which comprises administering to a patient in need thereof, an effective amount of a 1H-indazole-3-carboxamide derivative of general formula (I), in the form of a base or of an addition salt with an acid, or in the form of a hydrate or of a solvate of said base or acid addition salt.

8 Claims, No Drawings

INDAZOLECARBOXAMIDE DERIVATIVES FOR THE TREATMENT AND PREVENTION OF MALARIA

CROSS-REFERENCE TO RELATED APPLICATIONS

This application is a continuation of Patent Cooperation Treaty International Application PCT/FR2005/000612, filed on Mar. 15, 2005.

SUMMARY OF THE INVENTION

The invention relates to the use of 1H-indazole-3-carboxamide derivatives, and of their pharmaceutically acceptable salts, for preparing a medicinal product intended for the treatment and prevention of malaria.

BACKGROUND OF THE INVENTION

Malaria is a parasitic disease transmitted by mosquitoes of the anopheles type. This disease represents a major public health problem, with from 300 to 500 million individuals infected and 2.7 million deaths each year, largely children. Although it has been eradicated in many regions of the world, malaria continues to progress endemically in Africa, in South-East Asia and in South America, in particular due to resistance of the parasite to some of the molecules used as antimalarial medicinal products, in particular to chloroquine, which has for a long time been the most commonly used molecule.

Several species of *Plasmodium* are responsible for the transmission of malaria to humans, among which *Plasmodium falciparum* causes the lethal forms of the disease.

It therefore appears to be necessary to find novel molecules suitable for combating malaria, and in particular for combating *Plasmodium falciparum*.

1H-indazole-3-carboxamide derivatives are described in international application PCT/FR03/02862. That application discloses the inhibitory properties of these derivatives with respect to certain "cycline dependent kinases" (CDKS), such as CDK1, CDK2 and CDK4, and also the use of these derivatives for treating cancers, autoimmune and/or inflammatory diseases, cardiovascular diseases, neurodegenerative diseases, viral and fungal infections, degenerative diseases of the musculoskeletal system, haematological diseases, and kidney diseases and liver diseases due to toxins or to alcohol.

The applicant has now found that these 1H-indazole-3-carboxamide derivatives inhibit the growth of the *Plasmodium falciparum* parasite and are therefore useful for the treatment and prevention of malaria.

DETAILED DESCRIPTION OF THE INVENTION

A subject of the invention is the use of the compounds corresponding to general formula (I):

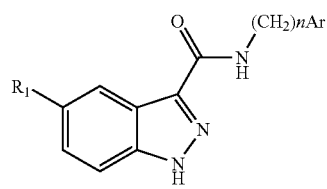

in which:

$R_1$ represents a hydrogen or a halogen atom, or a group —$NH_2$, —$NHR_2$, —$NHCOR_2$, —$NO_2$, —CN, —$CH_2NH_2$ or —$CH_2NHR_2$;

or else $R_1$ represents a phenyl optionally substituted with one or two substituents chosen, independently of one another, from halogen atoms and $C_{1-6}$ alkyl, $C_{1-6}$ alkoxy, —OH, —$NH_2$, —$NHR_2$ and —$NR_2R_3$ groups;

or else $R_1$ represents a heteroaromatic group optionally substituted with one or two substituents chosen, independently of one another, from halogen atoms and heteroaromatic, $C_{1-6}$ alkyl, —OH, —$NH_2$, —$NHR_2$, —$NHCOR_2$, —$COOR_2$, —$CONH_2$, —$CONHR_2$ and —$CH_2XR_2$ groups, where X is chosen from O, NH and S;

Ar represents a phenyl group optionally substituted with one or two substituents chosen, independently of one another, from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups;

or else Ar represents a heteroaromatic group optionally substituted with one or two substituents chosen, independently of one another, from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups;

$R_2$ and $R_3$, which may be identical to or different from one another, represent a $C_{1-6}$ alkyl group optionally substituted with a —$CONH_2$ group, with a phenyl group or with a heteroaromatic group;

or else $R_2$ and $R_3$, which may be identical to or different from one another, represent a phenyl group or a heteroaromatic group; and n is equal to 0, 1, 2 or 3, for preparing a medicinal product intended for the treatment and prevention of malaria.

The compounds of general formula (I) may contain one or more asymmetric carbon atoms. They may therefore exist in the form of enantiomers or of diastereoisomers. These enantiomers and diastereoisomers, and also mixtures thereof, including racemic mixtures, are part of the invention.

The compounds of general formula (I) may also exist in the form of tautomers. Thus, a subject of the invention is also the compounds of the invention in all their tautomeric forms.

The compounds of general formula (I) may exist in the form of bases or of addition salts with acids. Such addition salts are part of the invention.

These salts are advantageously prepared with pharmaceutically acceptable acids, but the salts of other acids that are useful, for example, for purifying or isolating the compounds of general formula (I) are also part of the invention.

The compounds of general formula (I) may also be in the form of hydrates or of solvates, i.e. in the form of associations or of combinations with one or more molecules of water or with a solvent. Such hydrates or solvates are also part of the invention.

In the context of the invention, and unless otherwise mentioned in the text, the term:

"$C_{t-z}$", where t and z can take the values of 1 to 6, is intended to mean a carbon chain comprising from t to z carbon atoms. For example, $C_{1-6}$ represents a carbon chain comprising from 1 to 6 carbon atoms;

"alkyl" is intended to mean a linear or branched, saturated aliphatic group. For example, a $C_{1-6}$ alkyl group represents a linear or branched carbon chain comprising from 1 to 6 carbon atoms, more particularly a methyl, ethyl, propyl, isopropyl, butyl, isobutyl, sec-butyl, tert-butyl, pentyl, etc.;

"alkoxy" is intended to mean an alkyloxy (—O-alkyl) group, the alkyl chain of which is saturated, and linear or branched;

"thioalkyl" is intended to mean an —S-alkyl group, the alkyl chain of which is saturated, and linear or branched;

"halogen atom" is intended to mean a fluorine, a chlorine, a bromine or an iodine;

"a heteroaromatic group" is intended to mean an aromatic group comprising between 5 and 9 carbon atoms and comprising between 1 and 4 hetero atoms, such as nitrogen, oxygen or sulphur. By way of examples of heteroaromatic groups, mention may be made of pyrrolyl, imidazolyl, pyrazolyl, triazolyl, tetrazolyl, thiazolyl, isothiazolyl, 1,3,4-thiadiazolyl, oxazolyl, isoxazolyl, oxadiazolyl, pyridinyl, pyridazinyl, pyrimidinyl, pyrazinyl, 1,3,5-triazinyl, indolyl, isoindolyl, indazolyl, benzimidazolyl, benzothiazolyl, quinolinyl, isoquinolinyl and pyrrolo[2,3-c]pyridinyl groups.

Among the compounds of general formula (I), one subgroup of compounds is such that $R_1$, $R_2$, $R_3$, Ar and n are as defined above, the following compounds being excluded:

N-phenyl-1H-indazole-3-carboxamide;
N-(2-chlorophenyl)-1H-indazole-3-carboxamide;
N-(3-chlorophenyl)-1H-indazole-3-carboxamide;
N-(4-chlorophenyl)-1H-indazole-3-carboxamide;
N-(2,4-dichlorophenyl)-1H-indazole-3-carboxamide;
N-(3,4-dichlorophenyl)-1H-indazole-3-carboxamide;
N-(2-methylphenyl)-1H-indazole-3-carboxamide;
N-(2-methoxyphenyl)-1H-indazole-3-carboxamide;
N-(4-methoxyphenyl)-1H-indazole-3-carboxamide;
N-(4-thiomethylphenyl)-1H-indazole-3-carboxamide;
N-(3-chloro-4-thiomethylphenyl)-5-amino-1H-indazole-3-carboxamide;
N-benzyl-1H-indazole-3-carboxamide;
N-(2-chlorobenzyl)-1H-indazole-3-carboxamide;
N-(4-methylbenzyl)-1H-indazole-3-carboxamide;
N-(pyridin-2-ylmethyl)-1H-indazole-3-carboxamide;
N-(pyridin-3-ylmethyl)-1H-indazole-3-carboxamide;
N-(pyridin-4-ylmethyl)-1H-indazole-3-carboxamide;
N-(2-phenylethyl)-1H-indazole-3-carboxamide;
N-(3,4-dimethoxyphenylethyl)-1H-indazole-3-carboxamide;
N-[3-(pyridin-2-yl)propyl]-1H-indazole-3-carboxamide;
N-[3-(2,6-dimethylphenyl)propyl]-5-nitro-1H-indazole-3-carboxamide.

Among the compounds of general formula (I), another subgroup of compounds is such that $R_1$, $R_2$, $R_3$, Ar and n are as defined above, with the proviso that:

when $R_1$ represents a hydrogen atom:
if n is equal to 0 and Ar is a phenyl, then this phenyl is necessarily substituted as defined above, the substituents methyl, methoxy, thiomethyl and chlorine atom being excluded;
if n is equal to 1 and Ar is a phenyl, then this phenyl is necessarily substituted as defined above, the substituents methyl and chlorine atom being excluded;
if n is equal to 1 and Ar is a pyridinyl, then this pyridinyl is necessarily substituted as defined above;
if n is equal to 2 and Ar is a phenyl, then this phenyl is necessarily substituted as defined above, the substituent methoxy being excluded;
if n is equal to 3 and Ar is a pyridinyl, then this pyridinyl is necessarily substituted as defined above;
when $R_1$ represents an —$NH_2$ group, n is equal to 0 and Ar is a phenyl, then the substituent(s) of the phenyl of Ar cannot be chosen from a thiomethyl or a chlorine atom;
when $R_1$ represents an —$NO_2$ group, n is equal to 3 and Ar is a phenyl, then the substituent(s) of the phenyl of Ar cannot be a methyl.

Another subgroup of compounds of formula (I) is such that $R_1$, $R_2$, $R_3$, Ar and n are as defined above, with the proviso that:

when $R_1$ represents a hydrogen atom:
then Ar represents a phenyl group substituted with one or two substituents chosen, independently of one another, from bromine or iodine atoms, and $C_{2-6}$ alkyl, $C_{2-6}$ thioalkyl, $C_{2-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups;

or else Ar represents a heteroaromatic group chosen from a pyrrolyl, imidazolyl, pyrazolyl, triazolyl, tetrazolyl, thiazolyl, isothiazolyl, 1,3,4-thiadiazolyl, oxazolyl, isoxazolyl, oxadiazolyl, pyridazinyl, pyrimidinyl, pyrazinyl, 1,3,5-triazinyl, indolyl, isoindolyl, indazolyl, benzimidazolyl, benzothiazolyl, quinolinyl, isoquinolinyl and pyrrolo[2,3-c]pyridinyl, said heteroaromatic group being optionally substituted with one or two substituent; or else Ar represents a pyridinyl substituted with one or two substituents; these substituents being chosen from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups;

when $R_1$ represents a halogen atom, or an —$NH_2$, —$NHR_2$, —$NHCOR_2$, —$NO_2$, —CN, —$CH_2NH_2$ or —$CH_2NHR_2$ group;

or else when $R_1$ represents a phenyl optionally substituted with one or two substituents chosen, independently of one another, from halogen atoms and $C_{1-6}$ alkyl, $C_{1-6}$ alkoxy, —OH, —$NH_2$, —$NHR_2$ and —$NR_2R_3$ groups;

or else when $R_1$ represents a heteroaromatic group optionally substituted with one or two substituents chosen, independently of one another, from halogen atoms and heteroaromatic, $C_{1-6}$ alkyl, —OH, —$NH_2$, —$NHR_2$, —$NHCOR_2$, —$COOR_2$, —$CONH_2$, —$CONHR_2$ and —$CH_2XR_2$ groups, where X is chosen from O, NH and S;

then Ar represents a phenyl group optionally substituted with one or two substituents chosen, independently of one another, from bromine or iodine atoms, and $C_{2-6}$ alkyl, $C_{2-6}$ thioalkyl, $C_{2-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups;

or else Ar represents a heteroaromatic group optionally substituted with one or two substituents, chosen, independently of one another, from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups.

Among the compounds of general formula (I), another subgroup of compounds is defined as follows:

when $R_1$ represents a hydrogen atom:

then Ar represents a phenyl substituted with one or two substituents chosen, independently of one another, from a bromine atom or a —$CH_2OH$, phenoxy, —$NH_2$, —$NHR_2$, —$NR_2R_3$, —CN, —$SO_2NH_2$, —COOH, —$COOR_2$ or —$CONH_2$ group;

or else Ar represents a heteroaromatic group chosen from imidazolyl, 1,3,4-thiadiazolyl, pyrazinyl, indolyl, indazolyl, quinolinyl or isoquinolinyl, said heteroaromatic group being optionally substituted with one or two substituents; or else Ar represents a pyridinyl substituted with one or two substituents; these substituents being chosen from halogen atoms (more particularly chlorine) and —COOH, $C_{1-6}$ alkyl (more particularly a methyl) and $C_{1-6}$ alkoxy (more particularly a methoxy) groups;

$R_2$ and $R_3$, which may be identical to or different from one another, represent a $C_{1-6}$ alkyl group (more particularly a methyl or an ethyl); or else $R_2$ and $R_3$ represent a phenyl; and n is equal to 0, 2 or 3;

when $R_1$ represents a halogen atom (more particularly a bromine or an iodine) or an —$NH_2$, —$NHCOR_2$, —$NO_2$, —CN or —$CH_2NH_2$ group;

or else when $R_1$ represents a phenyl;

or else when $R_1$ represents a heteroaromatic group (more particularly a pyrazolyl, tetrazolyl, thiazolyl, oxazolyl, pyridinyl, pyrimidinyl, quinolinyl, isoquinolinyl or pyrrolo[2,3-c]pyridinyl) optionally substituted with one or two substituents chosen, independently of one another, from halogen atoms (more particularly a chlorine or a fluorine) and heteroaromatic (more particularly a pyridinyl), $C_{1-6}$ alkyl (more particularly a methyl), —OH, —$NH_2$, —$NHR_2$, —$NHCOR_2$, —$COOR_2$, —$CONH_2$, —$CONHR_2$ and —$CH_2OR_2$ groups;

then Ar represents a phenyl group optionally substituted with one or two substituents chosen, independently of one another, from halogen atoms (more particularly a chlorine or a fluorine) and morpholinyl, —$CH_2$-morpholinyl, —$NHSO_2R_2$, —CN, —$SO_2R_2$, —$SO_2NH_2$, —$SO_2NHR_2$, —COOH, —$CONHNH_2$, —$CH_2NHR_2$ and —$CH_2NR_2R_3$ groups;

or else Ar represents a heteroaromatic group (more particularly a pyridinyl) optionally substituted with a $C_{1-6}$ alkoxy group, preferably a methoxy;

$R_2$ and $R_3$, which may be identical to or different from one another, represent a $C_{1-6}$ alkyl group (more particularly a methyl, ethyl or 2-methylpropyl) optionally substituted with a —$CONH_2$ group or with a phenyl group; or $R_2$ and $R_3$, which may be identical to or different from one another, represent a phenyl group or a heteroaromatic group, more particularly a pyridinyl or a pyrimidinyl; and n is equal to 0 or 1.

Among the compounds of general formula (I), another subgroup of compounds can also be defined as follows:

$R_1$ represents a heteroaromatic group optionally substituted with one or two substituents, chosen, independently of one another, from halogen atoms and heteroaromatic, $C_{1-6}$ alkyl, —OH, —$NH_2$, —$NHR_2$, —$NHCOR_2$, —$COOR_2$, —$CONH_2$, —$CONHR_2$ and —$CH_2XR_2$ groups, where X is chosen from O, NH and S; and/or Ar represents a phenyl group optionally substituted with one or two substituents chosen, independently of one another, from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups;

or else Ar represents a heteroaromatic group optionally substituted with one or two substituents chosen, independently of one another, from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups; and/or $R_2$ and $R_3$, which may be identical to or different from one another, represent a $C_{1-6}$ alkyl group optionally substituted with a —$CONH_2$ group, with a phenyl group or with a heteroaromatic group; or else $R_2$ and $R_3$, which may be identical to or different from one another, represent a phenyl group or a heteroaromatic group; and/or n is equal to 0, 1, 2 or 3.

Among the compounds of general formula (I) another subgroup of compounds can also be defined as follows:

$R_1$ represents a heteroaromatic group, more particularly a pyrazolyl, thiazolyl, tetrazolyl, oxazolyl, pyridinyl, isoquinolinyl or pyrrolo[2,3-c]pyridinyl, optionally substituted with one or two substituents chosen, independently of one another, from halogen atoms (more particularly chlorine) and heteroaromatic (more particularly a pyridinyl), $C_{1-6}$ alkyl (more particularly a methyl), —$NH_2$ and —$CONHR_2$ groups; and/or Ar represents a phenyl group optionally substituted with one or two substituents chosen, independently of one another, from —$NHSO_2R_2$, —CN, —$SO_2R_2$, —$SO_2NH_2$, —$SO_2NHR_2$ and —$CH_2NHR_2$ groups;

or else Ar represents a heteroaromatic group (more particularly a pyridinyl) optionally substituted with one or two substituents chosen, independently of one another, from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups; and/or $R_2$ and $R_3$, which may be identical to or different from one another, represent a $C_{1-6}$ alkyl group, more particularly a methyl or an ethyl, optionally substituted with a —$CONH_2$ group; or else $R_2$ and $R_3$, which may be identical to or different from one another, represent a phenyl group or a heteroaromatic group; and/or n is equal to 0 or 1.

The subject of the present invention is also the use, for preparing a medicinal product intended for the treatment and prevention of malaria, of any one of the subgroups of the compounds of formula (I) defined above.

Mention may in particular be made of the use, for preparing a medicinal product intended for the treatment and prevention of malaria, of one of the following compounds (the numbers in brackets refer to the numbers of the compounds in the table hereinafter):

N-(pyridin-4-yl)-5-isoquinolin-4-yl-1H-indazole-3-carboxamide (No. 3)

N-(pyridin-4-yl)-5-(1H-pyrrolo[2,3-c]pyridin-4-yl)-1H-indazole-3-carboxamide (No. 10)

5-(1H-pyrazol-4-yl)-N-(pyridin-4-yl)-1H-indazole-3-carboxamide (No. 11)

5-(6-chloropyridin-3-yl)-N-pyridin-4-yl-1H-indazole-3-carboxamide (No. 12)

N-{3-[(ethylamino)methyl]phenyl}-5-isoquinolin-4-yl-1H-indazole-3-carboxamide (No. 14)

N-{3-[(ethylamino)methyl]phenyl}-5-(1H-pyrrolo[2,3-c]pyridin-4-yl)-1H-indazole-3-carboxamide (No. 21).

The compounds of general formula (I) can be prepared by means of the methods illustrated in the schemes that follow, the operating conditions of which are conventional for those skilled in the art, as described in international application PCT/FR03/02862.

In the following text, the term "protective group PG" is intended to mean a group that makes it possible to prevent the reactivity of a function or position, in a chemical reaction which may affect it, and that restores this function or position after cleavage according to methods known to those skilled in the art. Examples of protective groups and also methods of protection and deprotection are given, inter alia, in *Protective groups in Organic Synthesis*, Green et al., 3rd Ed. (John Wiley & Sons, Inc., New York).

When $R_1$ represents a halogen atom, an —$NO_2$ group or a —CN group, the compounds of general formula (I) can be prepared by means of the method illustrated in scheme 1.

This method consists in converting an indole of general formula (II), where $R_1$ is an —$NO_2$, a —CN or a halogen atom, to an indazole-3-carbaldehyde of general formula (III), for example with nitrous acid. The compound of general formula (III) is then protected in a basic medium with a PG group, of the trimethylsilylethoxymethyl (SEM) or mesitylenesulphonyl (Mts) type, so as to give the indazole-3-carbaldehyde, protected in the 1-position, of general formula (IV). The compound (IV) is oxidized to indazole-3-carboxylic acid of general formula (V), for example by reaction with sodium chlorite. The indazole-3-carboxamide protected in the 1-position of general formula (VII) is obtained by coupling the compound of general formula (V) with an amine of general formula $Ar(CH_2)nNH_2$ (VI) in which Ar and n are as defined in general formula (I). This coupling reaction can be carried out by activation of a compound of general formula (V) with coupling reactants such as carbonyldiimidazole or isopropyl chloroformate or isobutyl chloroformate.

The compound of general formula (VII) can be deprotected either by the action of a base such as sodium hydroxide, or in the presence of tetrabutylammonium fluoride (TBAF) and of ethylenediamine, or alternatively in the presence of trifluoroacetic acid, and then heating with ethylene diamine. This deprotection step makes it possible to obtain the indazole-3-carboxamide of general formula (I).

When $R_1$ is a hydrogen atom, the method of preparation described in scheme 1 is reiterated, carrying out the coupling reaction for the amine of general formula $Ar(CH_2)nNH_2$ (VI), as defined above, with commercial indazole-3-carboxylic acid.

The compounds of general formula (I) where $R_1$ represents an —$NH_2$ are obtained by reduction of a compound of general formula (I), where $R_1$ is an —$NO_2$, as obtained according to scheme 1, for example in the presence of tin chloride.

The compounds of general formula (I) where $R_1$ represents an —$NHR_2$ or an —$NHCOR_2$ are obtained by functionalization of the corresponding compounds of general formula (I) where $R_1$ is an —$NH_2$, according to techniques known to those skilled in the art.

The compounds of general formula (I) where $R_1$ represents a —$CH_2NH_2$ are obtained by hydrogenation at atmospheric pressure of a compound of general formula (I) where $R_1$ is a —CN, as obtained according to scheme 1, for example in the presence of palladium-on-charcoal.

The compounds of general formula (I) where $R_1$ represents a —$CH_2NHR_2$ are obtained by functionalization of the corresponding compounds of general formula (I) where $R_1$ is a —$CH_2NH_2$, according to techniques known to those skilled in the art.

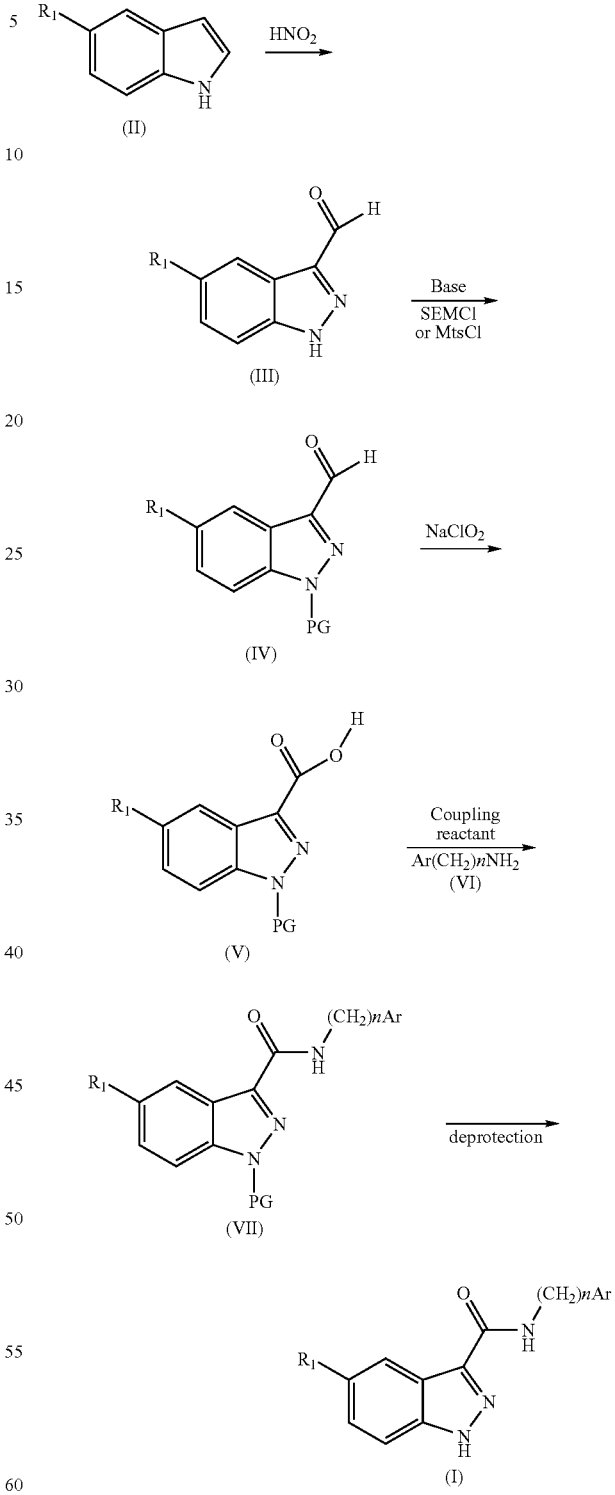

Scheme 1

When $R_1$ represents an optionally substituted phenyl or heteroaromatic group, the compounds of general formula (I) can be obtained according to one of the methods illustrated in schemes 1, 2 and 3. Moreover, when $R_1$ represents an oxazolyl group, the compounds of formula (I) can be obtained according to scheme 4, and when $R_1$ represents a thiazolyl group, the compounds of formula (I) can be obtained according to scheme 5.

In the case of schema 1, the compound of general formula (II), where $R_1$ represents an optionally substituted phenyl or heteroaromatic group as defined in general formula (I), can be obtained, for example, by means of a Suzuki-type reaction on 5-iodoindole according to techniques known to those skilled in the art.

Scheme 2 illustrates an alternative method for preparing the compound of general formula (VII) from 5-iodoindole.

The compound of general formula (IVa), where SEM is a trimethylsilylethoxymethyl group, is obtained by repeating the first two steps illustrated in scheme 1. A Suzuki reaction, carried out for example in the presence of a boronic acid of general formula $R_1B(OH)_2$ (VIII), where $R_1$ represents an optionally substituted phenyl or heteroaromatic group as defined in general formula (I), of an inorganic base, such as sodium carbonate ($Na_2CO_3$) and of palladium (0), makes it possible to obtain the compound of general formula (IV), in which PG represents an SEM group. The compound of general formula (I), where $R_1$ represents an optionally substituted phenyl or heteroaromatic group as defined in general formula (I), is obtained from the compound of general formula (IV) by repeating the last three steps illustrated in scheme 1.

Scheme 2

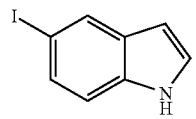

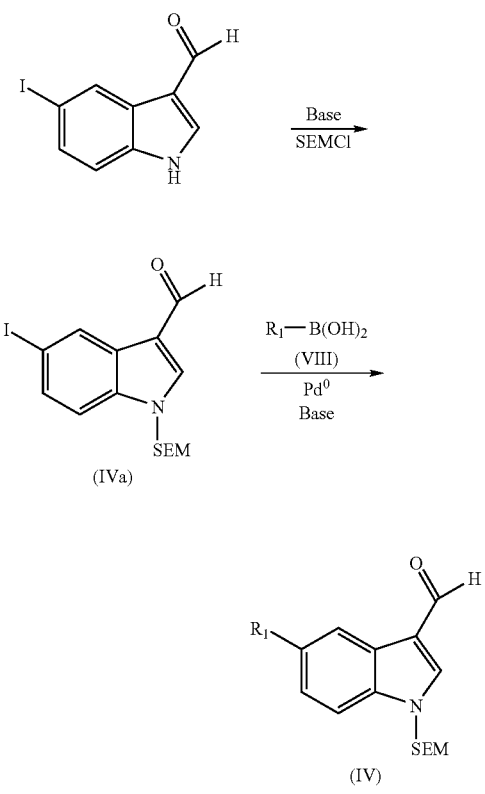

Scheme 3 illustrates a method of preparation from 5-iodoisatin or from 5-bromoisatin.

Scheme 3

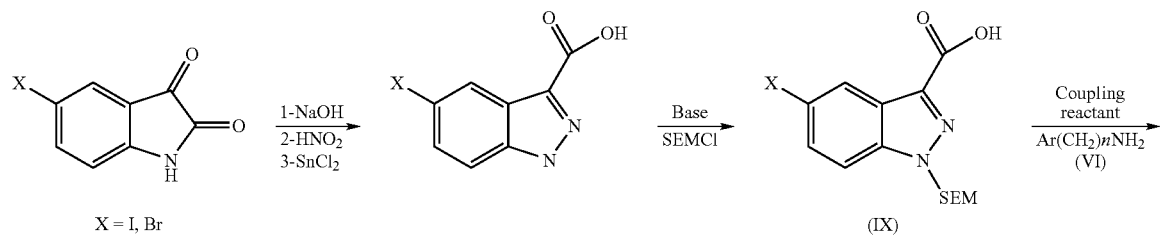

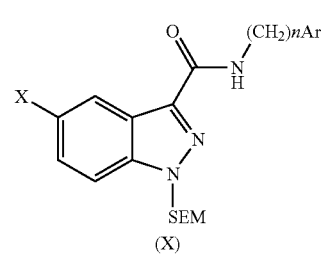

-continued

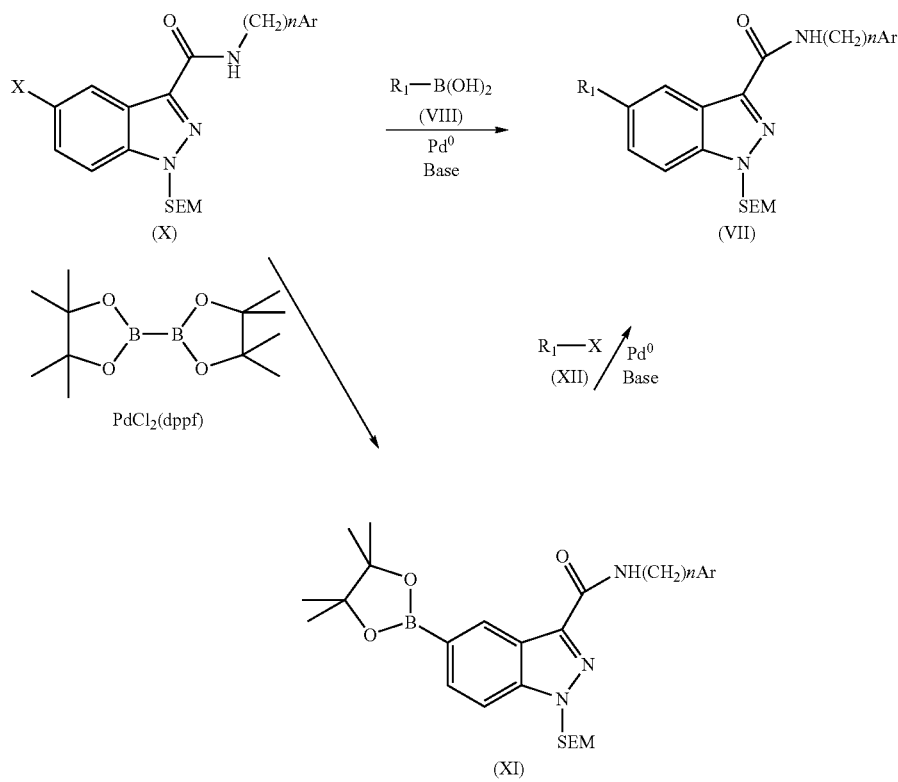

5-Iodo- or 5-bromoindazolecarboxylic acid can be obtained by opening the indoledione ring of the 5-iodoisatin or of the 5-bromoisatin, for example in the presence of sodium hydroxide, and then by diazotization, for example by means of nitrous acid, and, finally, by reduction and formation of the indazole ring, for example in the presence of tin chloride ($SnCl_2$). The 5-iodo- or 5-bromoindazole-3-carboxylic acid obtained is then protected in a basic medium, for example with an SEM group, so as to give the compound of general formula (IX), in which X represents a bromine or iodine atom.

The indazole-3-carboxamide of general formula (X) can be obtained by coupling the compound of general formula (IX) with an amine of general formula $Ar(CH_2)nNH_2$ (VI), in which Ar and n are as defined in general formula (I). This coupling reaction can be carried out by activation of a compound of general formula (IX) with coupling reactants, such as carbonyldiimidazole or isopropyl chloroformate or isobutyl chloroformate.

The compound of general formula (VII) can be obtained from the compound of general formula (X) by means of 2 methods:
  either by means of a Suzuki reaction, carried out in the presence of a boronic acid of general formula $R_1B(OH)_2$ (VIII), where $R_1$ represents an optionally substituted phenyl or heteroaromatic group as defined in general formula (I), of a base and of palladium (0);
  or by means of a dioxaborolane of general formula (XI) obtained by reaction of bis(pinacolato)diborane and of 1,1'-bis(diphenylphosphino)ferrocenedichloropalladiumII with the compound of general formula (X), the intermediate of general formula (XI) then being brought into the presence of an inorganic base, such as sodium acetate or potassium acetate, of palladium (0) and of a compound of general formula $R_1$—X (XII), where $R_1$ represents an optionally substituted phenyl or heteroaromatic group as defined in general formula (I) and X is a bromine or iodine atom.

The compound of general formula (I), where $R_1$ represents an optionally substituted phenyl or heteroaromatic group as defined in general formula (I), is obtained by deprotection of the compound of general formula (VII), as illustrated in the final step of scheme 1.

Scheme 4 illustrates a method for preparing the compounds of general formula (VIIa), i.e. the compounds of general formula (VII) for which $R_1$ represents an oxazolyl group and PG represents an SEM group.

The compound of general formula (X), as defined above and in which X represents an iodine atom, is formylated, for example in the presence of carbon monoxide and of a palladium complex, such as tetrakis(triphenylphosphine)palladium, and then of a reducing agent, such as tributyl tin hydride in a solvent, such as tetrahydrofuran (THF). The compound of general formula (XIII) thus obtained is refluxed in a solvent, such as methanol, in the presence of tosylmethyl isocyanate (TosMIC) and of a base such as potassium carbonate ($K_2CO_3$), so as to obtain the compound of general formula (VIIa).

The compound of general formula (I), where $R_1$ represents an oxazolyl group, is obtained from the compound of general formula (VIIa) by deprotection as illustrated in the final step of scheme 1.

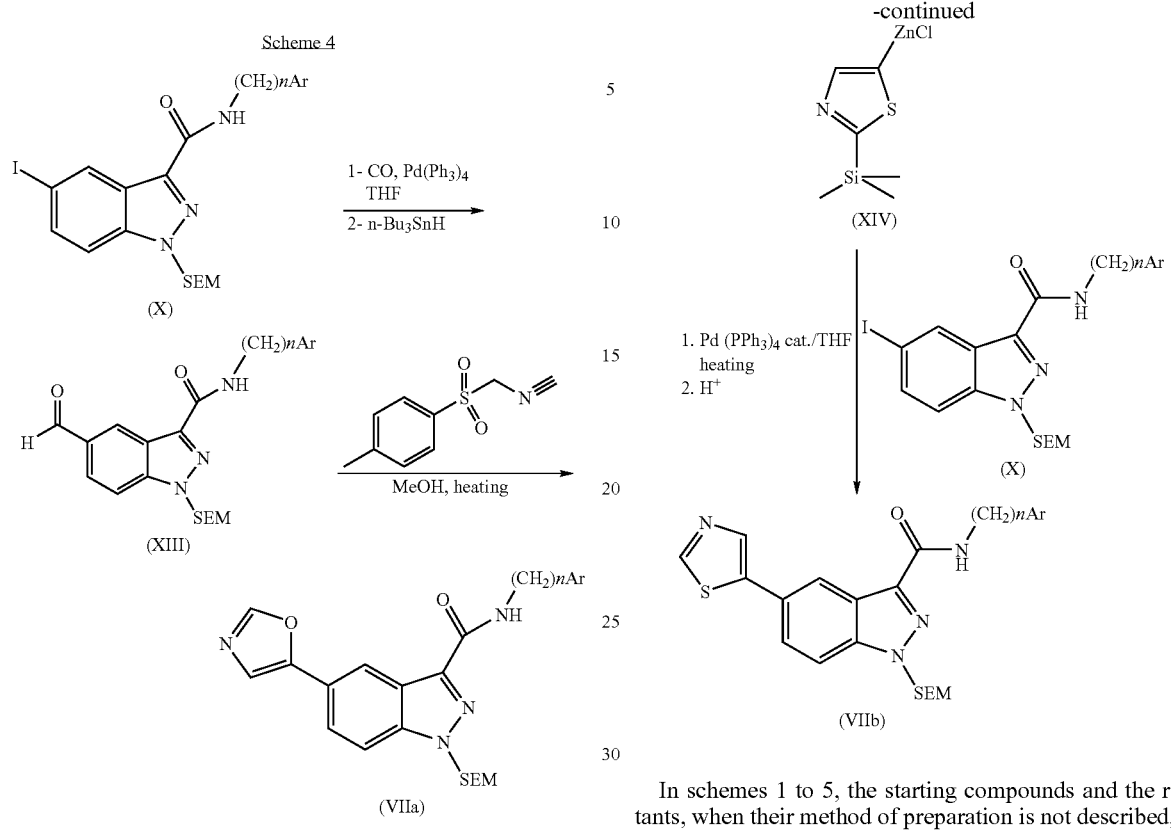

Scheme 5 illustrates a method for preparing the compounds of general formula (VIIb), i.e. the compound of general formula (VII) for which $R_1$ represents a thiazolyl group and PG represents an SEM group.

The thiazolyl group is introduced by heating the compound of general formula (X), as defined above and in which X represents an iodine atom, in the presence of the derivative of general formula (XIV) illustrated in scheme 5, and of tetrakis (triphenylphosphine)palladium in anhydrous THF, and then by acidification. The derivative of formula (XIV) is prepared from 2-trimethylsilyl(thiazole), in the presence of a strong base, such as butyllithium, by reaction of zinc chloride ($ZnCl_2$) in solution in anhydrous ether. The compound of general formula (VIIb) thus obtained is deprotected according to the final step of scheme 1, in order to obtain the compound of general formula (I), where $R_1$ represents a thiazolyl group.

Scheme 5

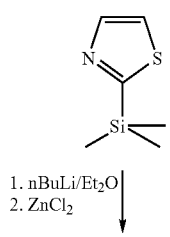

1. nBuLi/$Et_2O$
2. $ZnCl_2$

In schemes 1 to 5, the starting compounds and the reactants, when their method of preparation is not described, are commercially available or are described in the literature, or can be prepared by methods which are described therein or which are known to those skilled in the art.

The following examples describe the preparation of some compounds that can be used in accordance with the invention. These examples are not limiting and merely illustrate the invention.

The numbers of the compounds exemplified refer to those given in the table hereinafter. The microanalyses, the IR and NMR spectra and/or the LC/MS/UV (Liquid Chromatography coupled to Mass Spectroscopy and to Ultraviolet analysis) confirm the structures of the compounds obtained. For each LC/MS/UV value provided, the percentage in brackets represents the UV purity of the compound. As regards "Mp", it represents the melting point of the compounds obtained.

Example 1

Compound No. 1

N-(Pyridin-4-yl)-5-pyridin-3-yl-1H-indazole-3-carboxamide hydrochloride

Intermediate 1.1
5-Iodo-1H-indazole-3-carboxylic acid
5-Iodoisatin (5 g, 18.3 mmol) is heated in the presence of sodium hydroxide (0.77 g, 19.2 mmol in 12 ml of $H_2O$) until it is dissolved, and the reaction mixture is then cooled to 0° C. A solution of sodium nitrite precooled to 0° C. (1.26 g, 18.3 mmol in 5.5 ml of $H_2O$) is added. The paste obtained is added portionwise, with vigorous stirring, to a solution of sulphuric acid (3.40 g, 34.8 mmol in 37 ml of $H_2O$) precooled to 0° C. such that the temperature does not exceed 4° C. The stirring is maintained for 15 min and then a tin chloride solution (SnCl₂.2H₂O, 9.91 g, 43.9 mmol in 15 ml of concentrated HCl) is added slowly such that the temperature does not exceed 4° C. The mixture is left to react for several hours. The reaction mixture is filtered. The solid is washed with boiling water and then taken up with ethanol under hot conditions. The insoluble impurities are eliminated by filtration. 2 g of product are obtained.

Intermediate 1.2

Sodium 5-iodo-1-(2-trimethylsilylethoxymethyl)-1H-indazole-3-carboxylate

Intermediate 1.1 (20 g, 70 mmol) is added, at 0° C., under argon, to sodium hydride (6.16 g, 55% in oil, 140 mmol) in anhydrous THF (200 ml). The temperature is allowed to return to ambient temperature and the stirring is maintained for 20 min. The reaction mixture is again cooled to 0° C. and 2-(trimethylsilyl)ethoxymethyl chloride (12.25 g, 73.5 mmol) in solution in THF (75 ml) is introduced slowly. The reaction is stirred for a few minutes at 0° C. and then for 3 h at ambient temperature. 80 ml of water are added. The THF is evaporated off under vacuum and the insoluble material is filtered off. The solid is washed with H₂O and then with a diethyl ether/petroleum ether mixture and, finally, with diethyl ether. The solid obtained is dried under vacuum over potassium hydroxide. 20.71 g of product are obtained in the form of a yellow powder.

Intermediate 1.3

N-(Pyridin-4-yl)-5-iodo-1-(2-trimethylsilyl-ethoxymethyl)-1H-indazole-3-carboxamide A solution of isopropyl chloroformate in toluene (1M, 12 ml) is added, under argon, to a solution of intermediate 1.2 (5.02 g, 11.4 mmol) in anhydrous THF (50 ml), at a temperature of −10° C., followed dropwise by N-methylmorpholine (1.22 g, 12 mmol). The temperature is maintained at −10° C. for 5 min and the refrigerant bath is then removed. The mixture is stirred for 25 min at ambient temperature and then cooled again and a solution of 4-aminopyridine (1.13 g, 12 mmol) in THF is added. The reaction mixture is then stirred overnight at ambient temperature, filtered, and concentrated under vacuum. The crude product is chromatographed on silica gel (500 g), elution being carried out according to a gradient of CH₂Cl₂ with EtOAc. 4.17 g of product are obtained.

Intermediate 1.4

N-(Pyridin-4-yl)-5-pyridinyl-3-yl-1-(2-trimethylsilylethoxymethyl)-1H-indazole-3-carboxamide Pyridine-3-boronic acid (299 mg, 1.15 equiv.) and then an aqueous Na₂CO₃ solution (734 mg/2.7 ml H₂O, 5 equiv.) are added, under argon, to a solution of intermediate 1.3 (685 mg, 1.38 mmol) in dimethoxyethane (DME) (5.5 ml). The reactor is degassed several times with argon and then, under argon, tetrakis(triphenylphosphine)palladium (48 mg, 0.03 equiv.) is added. The reaction mixture is heated at 85° C. overnight. The solvents are evaporated off under vacuum and the residue is extracted with EtOAc/H₂O. The organic phase is dried and evaporated. The crude product is chromatographed on silica gel (200 g). Elution with EtOAc/MeOH (95/5) gives 370 mg of product, after evaporation.

N-(Pyridin-4-yl)-5-pyridin-3-yl-1H-indazole-3-carboxamide hydrochloride

A solution of tetrabutylammonium fluoride (TBAF) in THF (1M, 6 ml, 5 equiv.), water (0.2 ml) and ethylenediamine (0.20 ml, 3 mmol, 2.5 equiv.) are added, under argon, to a solution of intermediate 1.4 (530 mg, 1.19 mmol) in THF (15 ml). The reaction mixture is heated at 60° C. for 3 hours. A further addition of tetrabutylammonium fluoride (1N, 3 ml) is carried out. The heating is maintained for a further overnight period. The reaction mixture is acidified with 4N HCl (1.2 ml), concentrated under vacuum, and then diluted with H₂O. The precipitate is filtered off, and washed with CH₃OH and diethyl ether. The solid obtained is recrystallized from CH₂Cl₂/MeOH. 190 mg of product are obtained in the form of a white powder.

Mp: 196° C.

LC/MS/UV: MH+316 (96.8%)

¹H RMN (500 MHz, DMSO-D6) δ (ppm): 7.53 (dd, 1H), 7.84 (s, 2H), 7.99 (d, 2H), 8.13 (d, 1H), 8.46 (s, 1H), 8.50 (d, 1H), 8.59 (d, 1H), 8.92 (s, 1H), 10.86 (s, 1H), 14.1 (s, 1H).

Example 2

Compound No. 2

N-(Pyridin-4-yl)-5-(4-methyl-[3,4']-bipyridinyl-5-yl)-1H-indazole-3-carboxamide hydrochloride Intermediate 2.1

3,5-Dibromo-4-methylpyridine

A solution of n-butyllithium in hexane (1.6 N, 16 ml) is added dropwise, under argon, to a solution of diisopropylamine (3.6 ml, 1.02 equiv.) in anhydrous THF (145 ml) maintained at −10° C. The reaction mixture is cooled to −78° C. and then a solution of 3,5-dibromopyridine (5.92 g, 25 mmol) in THF (200 ml), cooled to −78° C., is added dropwise. The reaction mixture is stirred for 30 min and then methyl iodide (2.17 ml, 1.4 equiv.) is added dropwise. The stirring is maintained for 2 h at −78° C. A saturated aqueous NH₄Cl solution (120 ml) is added. After evaporation of the solvents, the reaction mixture is extracted with EtOAc. The organic phase is washed with brine, dried over MgSO₄ and evaporated. The yellow solid obtained is taken up with EtOAc. The suspension is filtered. The filtrate is evaporated and the residue is chromatographed on silica gel, elution being carried out with a petroleum ether/EtOAc (97.5/2.5) mixture. 1.67 g of product are obtained in the form of a white solid.

Intermediate 2.2

5-Bromo-4-methyl-[3,4']-bipyridinyl

Pyridine-4-boronic acid pinacolic ester (910 mg, 4.45 mmol), an aqueous Na₂CO₃ solution (2.35 g/9 ml H₂O) and, finally, tetrakis(triphenylphosphine)palladium (153 mg) are added, under argon, to a solution of intermediate 2.1 (1.3 g, 5.18 mmol) in DME (18 ml). The mixture is heated at 85° C. for 2 days. The solvent is evaporated off and the residue is then extracted with EtOAc/H₂O. The compound obtained after washing the organic solution with brine, drying over MgSO₄ and evaporation is chromatographed on silica gel (200 g), elution being carried out with an EtOAc/petroleum ether (1/1) mixture. 440 mg of product were obtained in the form of an oil.

Intermediate 2.3

N-(Pyridin-4-yl)-5-(4,4,5,5-tetramethyl-[1,3,2]-dioxaborolan-2-yl)-1-(2-trimethylsilylethoxymethyl)-1H-indazole-3-carboxylic acid A mixture of intermediate 1.3 (3.77 g, 7.6 mmol), of bis(pinacolato)diborane (2.12 g, 8.3 mmol) and of potassium acetate (2.24 g) in dimethyl sulphoxide (DMSO) (50 ml) is degassed with argon. 1,1'-Bis(diphenyl-phosphino)ferrocenedichloropalladiumII (310 mg, 0.38 mmol, 0.05 equiv.) is added under argon. The reaction mixture is heated at 80° C. for 1 h 30 min. Extraction with EtOAc/H₂O makes it possible to isolate an orange oil which is chromatographed on silica gel, elution being carried out with EtOAc. The yellow oil obtained is crystallized from diethyl ether. 2.56 g of product are obtained in the form of a white powder.

Intermediate 2.4

N-(Pyridin-4-yl)-5-(4-methyl-[3,4']-bipyridinyl-5-yl)-1-(2-trimethylsilylethoxymethyl)-1H-indazole-3-carboxamide An aqueous $Na_2CO_3$ solution (686 mg/2.6 ml) is added to a solution of intermediate 2.3 (640 mg, 1.29 mmol) and of intermediate 2.2 (370 mg, 1.15 equiv.) in DME (6 ml). The reaction mixture is degassed with argon.

Tetrakis(triphenylphosphine)palladium (46 mg) is added under argon. The reaction mixture is heated at 85° C. overnight. The solvent is evaporated off. Extraction with EtOAc/$H_2O$ makes it possible to isolate an oil which is crystallized from an EtOAc/petroleum ether mixture. 530 mg of product are obtained in the form of a white powder.

N-(Pyridin-4-yl)-5-(4-methyl-[3,4']-bipyridinyl-5-yl)-1H-indazole-3-carboxamide hydrochloride Cleavage of the SEM protective group of intermediate 2.4 is carried out in the presence of tetrabutylammonium fluoride in a manner similar to the procedure described in Example 1. The crude product is taken up in $MeOH/Et_2O$. The compound obtained is isolated by filtration and washed with MeOH. 265 mg of product are obtained in the form of a powder.

Mp: 192° C.

LC/MS/UV: MH+407 (96.1%)

$^1$H RMN (500 MHz, DMSO-D6) δ (ppm): 2.13 (s, 3H), 7.65 (m, 3H), 7.90 (d, J=8.5, 1H), 8.01 (d, J=7.2, 2H), 8.32 (s, 1H), 8.54 (s, 1H), 8.55 (d, J=6.2, 2H), 8.60 (s, 1H), 8.79 (d, J=5.7, 2H), 10.90 (s, 1H), 13 (s, 1H).

Example 3

Compound No. 3

N-(Pyridin-4-yl)-5-isoquinolin-4-yl-1H-indazole-3-carboxamide

Intermediate 3.1

5-Iodo-1H-indazole-3-carbaldehyde 1 g of sodium nitrite (27.6 g, 400 mmol) is added portionwise, under argon, to a suspension of 5-iodoindole (9.722 g, 40 mmol) in water, followed dropwise by a 6N HCl solution (59 ml). The temperature of the reaction mixture is maintained below 15° C. and the reaction mixture is then left at ambient temperature overnight, with vigorous stirring. The nitrous vapours are expelled under a stream of argon, and the reaction mixture is then filtered. Washing the solid with $H_2O$ followed by purification on silica gel (600 g), elution being carried out according to an elution gradient from $CH_2Cl_2$ to a $CH_2Cl_2/EtOAc$ (9/1) mixture, makes it possible to isolate 1.37 g of product in the form of a brown solid.

LC/MS/UV: MH+273 (88.6%)

Intermediate 3.2

5-Iodo-1-(2-trimethylsilylethoxymethyl)-1H-indazole-3-carbaldehyde

Intermediate 3.1 (2.58 g, 9.5 mmol) followed, dropwise, by a solution of trimethylsilylethoxymethyl chloride (SEMCl, 1.60 g, 9.6 mmol) in DMF (5 ml) are added, under argon, to a suspension of sodium hydride (50% in oil, 0.50 g, 10.4 mmol) in anhydrous DMF (10 ml). The stirring is maintained for 1 h at ambient temperature. Water is added and then the DMF is evaporated off under vacuum. The residue is taken up in $CH_2Cl_2$. The organic solution is washed with brine, dried, and then evaporated under vacuum. The crude product is chromatographed on silica gel (500 g). Elution with $CH_2Cl_2$ gives the product in the form of a viscous brown oil.

Intermediate 3.3

5-Isoquinolin-4-yl-1-(2-trimethylsilylethoxymethyl)-1H-indazole-3-carbaldehyde

Isoquinolin-4-ylboronic acid hydrochloride (0.56 g, 2.66 mmol), an aqueous $Na_2CO_3$ solution (1.42 g, 13.4 mmol in 5 ml $H_2O$) and tetrakis(triphenylphosphine)palladium0 (0.160 g, 0.14 mmol, 0.05 equiv.) are added, under argon, to a solution of intermediate 3.2 (1.07 g, 2.66 mmol) in DME (10 ml). The reaction mixture is heated by means of an oil bath regulated at 85° C. for 5 h, and is then concentrated under vacuum. The residue is taken up in EtOAc. The organic solution is washed with brine, dried, and then evaporated, to give a crude product which is purified on silica gel (150 g). Elution according to a gradient ranging from $CH_2Cl_2$ to $CH_2Cl_2/EtOAc$ (9/1) gives 0.84 g of product.

Intermediate 3.4

5-Isoquinolin-4-yl-1-(2-trimethylsilylethoxymethyl)-1H-indazole-3-carboxylic acid 2-Methyl-2-butene (5 ml), DMF (5 ml), and then an aqueous solution (10 ml) of sodium chlorite (1.12 g) and of sodium dihydrogen phosphate (1.37 g, in hydrate form) are added to a solution of intermediate 3.3 (0.50 g, 1.24 mmol) in DMF (5 ml) maintained at a temperature of between 0° C. and −5° C., cooled by means of a bath consisting of a mixture of ice and of salt. The temperature of the reaction mixture is maintained at 0° C. for 30 min, and the reaction mixture is then stirred for 4 h 30 min at ambient temperature and, after acidification with 6N HCl (5 ml), overnight. The reaction mixture is evaporated. The residue is taken up in EtOAc. This solution is washed with $H_2O$ and brine, dried over $Na_2SO_4$ and evaporated, to give 0.50 g of product in the form of a white solid.

Intermediate 3.5

N-(Pyridin-4-yl)-5-isoquinolin-4-yl-1-(2-trimethylsilylethoxymethyl)-1H-indazole-3-carboxamide Isopropyl chloroformate (1M in toluene, 1.2 ml) and N-methylmorpholine (0.120 g, 1.2 mmol) are added, under argon, to a solution of intermediate 3.4 (0.50 g, 1.19 mmol) in anhydrous THF (10 ml) maintained at a temperature of between −5° C. and 0° C. The reaction mixture is left to react for 15 min before adding 4-aminopyridine (0.114 g, 1.2 mmol). The reaction mixture is stirred for 30 min at 0° C. and then overnight at ambient temperature. It is then evaporated and taken up in EtOAc. The organic solution is washed with brine, dried over $Na_2SO_4$ and evaporated. The oil obtained is purified on silica gel. Elution with a $CH_2Cl_2/MeOH$ (9/1) mixture makes it possible to isolate 250 mg of product in the form of a yellow oil.

N-(Pyridin-4-yl)-5-isoquinolin-4-yl-1H-indazole-3-carboxamide

A mixture of intermediate 3.5 (0.250 g, 0.5 mmol), of 1,2-diaminoethane (0.150 g, 2.5 mmol) and of tetrabutylammonium fluoride in THF (1M, 5 ml) is heated, under argon, at 70° C. overnight. The reaction mixture is evaporated under vacuum. The residue is taken up with EtOAc. This solution is washed with a saturated aqueous solution of $NaHCO_3$ and brine, and then dried and evaporated. The solid obtained is washed with diethyl ether and then purified on silica gel (50 g). The compound obtained is eluted with an EtOAc/MeOH (9/1) mixture. It is taken up in a diethyl ether/petroleum ether mixture, and then filtered. 182 mg of product are obtained in the form of a white solid.

Mp: >250° C.

LC/MS/UV: MH+366 (99.4%)

$^1$H NMR (500 MHz, DMSO-D6) δ (ppm): 7.65 (d, J=8.5, 1H), 7.76 (t, J=7.3, 1H), 7.81 (t, J=7.4, 1H), 7.88 (dd, J=8.4, J=3.3, 2H), 7.92 (d, J=6.1, 2H), 8.26 (d, J=8.0, 1H), 8.34 (s, 1H), 8.46 (d, J=5.9, 2H), 8.52 (s, 1H), 9.38 (s, 1H), 10.85 (s, 1H), 14.2 (s, 1H).

Example 4

Compound No. 9

N-(Pyridin-4-yl)-5-(1,3-thiazol-5-yl)-1H-indazole-3-carboxamide

Intermediate 4.1
N-Pyridin-4-yl-5-(1,3-thiazol-5-yl)-(2-trimethylsilylethoxymethyl)-1H-indazole-3-carboxamide A solution of 2-trimethylsilyl(thiazole) (1.97 ml, 12 mmol) in anhydrous diethyl ether (12 ml) is added dropwise, under an argon atmosphere, to a solution of n-butyllithium (8.25 ml, 1.6 N in hexane, 13.2 mmol) in anhydrous diethyl ether (12 ml) cooled to −78° C. The stirring is maintained for 30 min at −78° C. and then a molar solution of $ZnCl_2$ (4.91 g, 36 mmol) in anhydrous diethyl ether (36 ml), freshly prepared from very dry $ZnCl_2$, is added. The refrigerant bath is removed and the mixture is stirred for 30 min at ambient temperature. The solvents are evaporated off under vacuum. A mixture of intermediate 1.3 (5.37 g, 12 mmol) and of tetrakis(triphenylphosphine)palladium (277 mg) in anhydrous THF (50 ml) is added to the residue, under argon, and the suspension is refluxed for 24 h. The reaction mixture is acidified to pH 2 by the addition of 1N HCl, and is then concentrated under vacuum. 1N sodium hydroxide is added so as to obtain a pH of 10. The solid obtained is stirred in the presence of $CH_2Cl_2$ and the zinc salts are separated by filtration. The filtrate is washed with water. The organic phase is dried over $MgSO_4$ and then evaporated. The brown oil obtained (5.10 g) is filtered rapidly through silica. After crystallization from diethyl ether, a yellow solid (2.40 g) is obtained. This solid chromatographed on silica (300 g). An elution gradient of petroleum ether/EtOAc (2/3) to petroleum ether/EtOAc (1/3) makes it possible to separate two isomers. The expected compound is the most polar. 1.08 g of product are obtained in the form of a white powder.

N-Pyridin-4-yl-5-(1,3-thiazol-5-yl)-1H-indazole-3-carboxamide

This compound is obtained by cleavage of the SEM protective group of intermediate 4.1 (452 mg, 1 mmol). The crude product is recrystallized from a MeOH/EtOAc mixture in the presence of a trace of water, and is then filtered. 22.5 g of product are obtained in the form of a yellow solid.

Mp: >250° C.
LC/MS/UV: MH+322 (98.5%)
$^1$H NMR (500 MHz, DMSO-D6) δ (ppm): 7.77 (d, J=8.8 Hz, 1H), 7.86 (d, J=8.8 Hz, 1H), 7.93 (d, J=6.3 Hz, 3H), 8.35 (s, 1H), 8.41 (s, 1H), 8.47 (d, J=6.3 Hz, 2H), 9.10 (s, 1H), 10.80 (s, 1H), 14.0 (s, 1H).

Example 5

Compound No. 10

N-(Pyridin-4-yl)-5-(1H-pyrrolo[2,3-c]pyridin-4-yl)-1H-indazole-3-carboxamide

Intermediate 5.1
3-Nitropyridin-4-ol

A nitric acid solution ($HNO_3$>90%, 13.3 ml) is added slowly to a solution of oleum ($H_2SO_4$ containing 20% $SO_3$, d=1.9, 10.5 ml) cooled to 0° C. 4-Pyridol nitrate (10 g, 63 mmol) is added, at 0° C., to the mixture, which is then heated at 90° C. for 1 h 30 min. The reaction mixture is poured over 50 g of ice. The suspension is stirred for 30 min at 0° C. and is then filtered. The solid is washed with a few ml of water and then air-dried. 6.59 g of product are obtained in the form of a white powder.

Intermediate 5.2
3-Bromo-5-nitropyridin-4-ol

Bromine (5.07 g, 31.7 mmol) is added dropwise to a suspension of intermediate 5.1 (4.04 g, 28.4 mmol) in $H_2O$ (40 ml). The mixture is heated with an oil bath at a temperature of 90° C. for 1 h. After cooling, the mixture is filtered. The solid is washed with $H_2O$ and then dried in a desiccator in the presence of silica gel. 4.51 g of product are obtained in the form of a white solid.

Intermediate 5.3
3-Bromo-4-chloro-5-nitropyridine

Intermediate 5.2 (5.30 g, 24.0 mmol) is dried at 60° C. under vacuum (0.5 mbar) for 2 h in a two-necked round-bottomed flask. $PCl_5$ (9.12 g, 43.8 mmol) and $POCl_3$ (0.5 ml, 5.4 mmol) are added. The mixture is heated to 160° C. with an oil bath. After 20 min, the solid has been converted to a clear brown oil. After cooling, the mixture solidifies. The volatile substances are evaporated off under vacuum and the solid, suspended in $CHCl_3$, is then treated at 0° C. with an aqueous potassium acetate solution (25 g KOAc/35 ml $H_2O$). The organic phase is separated and is then evaporated. The residue is extracted with a diethyl ether/$NaHCO_3$ mixture. The organic phase is washed with brine, dried over $Na_2SO_4$ and evaporated. The residue is taken up in $CH_2Cl_2$. The insoluble material is removed by filtration and the filtrate is evaporated, to give the expected product. 4.66 g of product are obtained in the form of a brown oil.

Intermediate 5.4
Diethyl (3-bromo-5-nitropyridin-4-yl)malonate

Diethyl malonate (7.2 ml, 47.4 mmol) is added, under nitrogen, to a suspension of NaH (1.70 g, 55-60% in oil, 39-46 mmol) in anhydrous DMF (30 ml), over 10-15 min, such that the temperature of the reaction mixture does not exceed 50° C. The stirring is maintained for a further 30 min after the addition. Intermediate 5.3 (4.46 g, 18.62 mmol) is added in solid form in small portions. The stirring is maintained for 3 h 30 min at ambient temperature. Water (50 ml) and AcOH (5 ml) are added. The mixture is extracted with diethyl ether. The organic phase is washed with brine, dried over $Na_2SO_4$ and evaporated. The residue is eluted on silica gel (300 g) according to a gradient from an EtOAc/petroleum ether (1/9) mixture to an EtOAc/petroleum ether (3/7) mixture. 5.15 g of product are obtained in the form of a brown oil.

Intermediate 5.5
3-Bromo-4-methyl-5-nitropyridine

Intermediate 5.4 (5.15 g, 14.2 mmol) is heated at 100° C. in the presence of 18% aqueous HCl (50 ml) for 15 h. The mixture is extracted with diethyl ether (3×80 ml). The ethereal solution is washed with brine, dried over $MgSO_4$ and evaporated under vacuum, to give the expected product. 2.43 g of product are obtained in the form of a yellow solid.

Intermediate 5.6
2-(3-Bromo-5-nitropyridin-4-yl)-N,N-dimethyl-ethylene-amine

A mixture of intermediate 5.5 (1.136 g, 5.19 mmol) and of DMF diethyl acetal (1.46 ml, 8.52 mmol) in DMF (6 ml) is heated at 85° C. for 1 h 15 min. The DMF is evaporated off under vacuum, to give the expected product. 1.407 g of product are obtained in the form of a purple-coloured solid.

Intermediate 5.7

4-Bromo-1H-pyrrolo[2,3-c]pyridine

Intermediate 5.6 (1.407 g, 5.13 mmol) in solution in acetic acid (15 ml) is heated under nitrogen in the presence of iron (powder 325 mesh, 1.85 g, 33.1 mmol) at 120° C. for 40 min. The mixture is filtered. The iron salts are washed with AcOH (5 ml). The filtrate is diluted in 75 ml of water, to give a clear, orangey-red-coloured solution. This solution is neutralized by the addition of solid $K_2CO_3$ until pH 9 is obtained. The brownish suspension is extracted with $CHCl_3$. The organic solution is washed with brine, filtered through a 0.45 μm membrane, dried over $Na_2SO_4$ and, finally, evaporated under vacuum. 801 mg of product are obtained in the form of a greyish-brown solid.

Intermediate 5.8

N-(Pyridin-4-yl)-5-(1H-pyrrolo[2,3-c]pyridin-4-yl)-1-(2-trimethylsilylethoxymethyl)-1H-indazole-3-carboxamide The synthesis of this intermediate is carried out in a similar manner to the synthesis of intermediate 2.4, performing a Suzuki reaction between intermediate 5.7 and intermediate 2.3 on a 2.43 mmol scale. The crude product is purified on silica gel (50 g), elution being carried out with an EtOAc/MeOH (95/5) mixture. 780 mg of product are obtained in the form of a white powder.

N-(Pyridin-4-yl)-5-(1H-pyrrolo[2,3-c]pyridin-4-yl)-1H-indazole-3-carboxamide

This compound is obtained by cleavage of the SEM protective group of intermediate 5.8 (780 mg, 1.61 mmol) with TFA, followed by heating in the presence of ethylenediamine. The crude product is stirred for 1 h in the presence of MeOH and is then filtered. 480 mg of product are obtained in the form of a white powder.

Mp: >250° C.

LC/MS/UV: MH+355 (100%)

$^1$H NMR (500 MHz, DMSO-D6) δ (ppm): 6.67 (s, 1H), 7.71 (s, 1H), 7.84 (s, 2H), 7.93 (d, J=5.7 Hz, 2H), 8.27 (s, 1H), 8.46 (d, J=6.3 Hz, 2H), 8.55 (s, 1H), 8.77 (s, 1H), 10.79 (s, 1H), 11.80 (s, 1H), 12-14 (s, 1H)

Example 6

Compound No. 15

5-(5-Amino-4-methylpyridin-3-yl)-N-pyridin-4-yl-1H-indazole-3-carboxamide

Intermediate 6.1

3-Bromo-4-methyl-5-aminopyridine

This compound is obtained by reduction of 3-bromo-4-methyl-5-nitropyridine (intermediate 5.5) with iron in a manner similar to the synthesis of intermediate 5.7, on a 10 mmol scale. 1.20 g of product are obtained in the form of a cream-coloured solid.

Intermediate 6.2

5-(5-Amino-4-methylpyridin-3-yl)-N-pyridin-4-yl-1-(2-trimethylsilylethoxymethyl)-1H-indazole-3-carboxamide The synthesis of this intermediate is carried out in a manner similar to the synthesis of intermediate 2.4, performing a Suzuki reaction between intermediate 6.1 and intermediate 2.3 on a 2.48 mmol scale. The reaction mixture is evaporated. The residue is taken up with $EtOAc/H_2O$. An insoluble material separates. After stirring for 1 h, it is filtered off. 1.02 g of product are obtained in the form of a cream-coloured powder.

5-(5-Amino-4-methylpyridin-3-yl)-N-pyridin-4-yl-1H-indazole-3-carboxamide

Intermediate 6.2 (980 mg, 2.06 mmol) in solution in THF (30 ml) is reacted with a solution of tetrabutylammonium fluoride (1M solution in THF, 10.3 ml), ethylenediamine (0.347 ml, 5.2 mmol) and $H_2O$ (0.377 ml). The mixture is heated at 60° C. for 3 days and then evaporated. The residue is stirred in an $EtOAc/H_2O$ mixture and is then filtered. The solid thus recovered is stirred in the presence of MeOH and is then filtered, to give the expected product (270 mg) in the form of a cream-coloured solid. The filtrate is evaporated under vacuum and is then chromatographed on silica gel (50 g), elution being carried out with an $MeOH/CH_2Cl_2$ (1/4) mixture, to give a 2nd batch of the expected product (1.5 g) in the form of a yellow-coloured solid.

LC/MS/UV: MH+345 (100%)

$^1$H NMR (500 MHz, DMSO-D6) δ (ppm): 1.98 (s, 3H), 5.19 (s, 2H), 7.40 (d, J=8.2 Hz, 1H), 7.67 (s, 1H), 7.74 (d, J=8.8 Hz, 1H), 7.91 (d, J=6.3 Hz, 2H), 7.96 (s, 1H), 8.08 (s, 1H), 8.45 (d, J=6.3 Hz, 2H), 10.76 (s, 1H), 13.67 (s, 1H)

Example 7

Compound No. 11

5-(1H-Pyrazol-4-yl)-N-(pyridin-4-yl)-1H-indazole-3-carboxamide

Intermediate 7.1

4-Iodo-1-(2-trimethylsilylethoxymethyl)-1H-pyrazole

Diisopropylethylamine (DIEA, 1.75 ml, 10 mmol) and trimethylsilylethoxymethyl chloride (SEMC1, 1.83 ml, 10 mmol) are added, under argon, to a solution of 4-iodopyrazole (1.94 g, 10 mmol) in $CH_2Cl_2$ (100 ml). The mixture is stirred overnight at ambient temperature. The solvent is evaporated off under vacuum. The residue is taken up with a diethyl ether/water mixture. The organic phase, after drying and evaporation, gives a colourless oil which is purified by elution on silica gel with an $EtOAc/CH_2Cl_2$ (5/95) mixture. 3.02 g of product are obtained in the form of a colourless oil.

Intermediate 7.2

N-(Pyridin-4-yl)-1-(2-trimethylsilylethoxymethyl)-5-[1-(2-trimethylsilylethoxymethyl)-1H-pyrazol-4-yl]-1H-indazole-3-carboxamide The synthesis of this intermediate is carried out in a manner similar to the synthesis of intermediate 2.4, performing a Suzuki reaction between intermediate 7.1 and intermediate 2.3 on a 2.0 mmol scale. The crude product is purified on silica gel (50 g), elution being carried out with an $MeOH/CH_2Cl_2$ (2/98) mixture. The purified compound is crystallized from a $CHCl_3/Et_2O$ mixture. 367 mg of product are obtained in the form of a white powder.

5-(1H-Pyrazol-4-yl)-N-(pyridin-4-yl)-1H-indazole-3-carboxamide

This compound is obtained by cleavage of the SEM protective groups of intermediate 7.2 (550 mg, 0.97 mmol) with TFA, followed by heating in the presence of ethylenediamine. The reaction mixture is filtered. The solid is stirred in the presence of $CHCl_3/H_2O$. The insoluble fraction is stirred in the presence of MeOH for 1 h and is then filtered, to give the expected product. 220 mg of product are obtained in the form of a white powder.

Mp: >250° C.

LC/MS/UV: MH+305 (100%)

$^1$H NMR (500 MHz, DMSO-D6) δ (ppm): 7.67 (d, J=8.2 Hz, 1H), 7.75 (d, J=6.9 Hz, 1H), 7.94 (d, J=6.3 Hz, 2H), 7.96 (broad s, 1H), 8.21 (broad s, 1H), 8.35 (s, 1H), 8.46 (d, J=5.7 Hz, 2H), 10.72 (s, 1H), 13.0 (s, 1H)

Example 8

Compound No. 13

5-(1,3-Oxazol-5-yl)-N-(pyridin-4-yl)-1H-indazole-3-carboxamide

Intermediate 8.1

5-Formyl-N-(pyridin-4-yl)-1(2-trimethylsilylethoxymethyl)-1H-indazole-3-carboxamide A stream of carbon monoxide is introduced, over 15 min, into a solution of intermediate 1.3 (4.95 g, 10 mmol) in THF (50 ml). Tetrakis(triphenylphosphine)palladium (578 mg, 0.5 mmol) is added and then a stream of carbon monoxide is introduced for 10 min. The mixture is brought to 50° C. and a solution of tributyltin hydride (3.05 ml, 11 mmol) in THF (20 ml) is added slowly over 2 h 30 min. After cooling, water (0.5 ml) is added and the reaction mixture is evaporated. The residue is purified on silica gel, elution being carried out with MeOH/EtOAc/$CH_2Cl_2$ (2/29/69). 2.65 g of product are obtained in the form of a yellow solid.

Intermediate 8.2

5-(1,3-Oxazol-5-yl)-N-(pyridin-4-yl)-1-(2-trimethylsilylethoxymethyl)-1H-indazole-3-carboxamide $K_2CO_3$ (1.02 g, 7.35 mmol) and tosylmethyl isocyanate (TosMIC, 1.44 g, 7.35 mmol) are added to intermediate 8.1 (2.65 g, 6.68 mmol) in solution in MeOH (100 ml). The mixture is refluxed for 2 h 30 min, and then, after cooling, it is concentrated under vacuum. The residue is taken up with EtOAc/$H_2O$. After drying and evaporation, the organic phase gives a solid which is purified on silica gel, elution being carried out with MeOH/EtOAc/$CH_2Cl_2$ (3/28.5/68.5). The purified product is recrystallized from EtOAc. 2.345 g of product are obtained in the form of a white solid.

5-(1,3-Oxazol-5-yl)-N-(pyridin-4-yl)-1H-indazole-3-carboxamide

Intermediate 8.2 (360 mg, 0.82 mmol) is reacted at ambient temperature with TFA (3 ml) for 1 h. The reaction mixture is evaporated under vacuum. The residue is taken up with THF, resulting in the separation of a solid. The mixture is again evaporated and then taken up in THF (10 ml). Ethylenediamine (267 µl, 4 mmol) is added and the mixture is heated at 70° C. overnight. The THF is evaporated off. The residue is triturated in MeOH, filtered, and then washed with diethyl ether. It is taken up with 80 ml of an MeOH/$H_2O$ (9/1) mixture. The mixture is refluxed. DMF is added until complete dissolution. After cooling, an orange solid appears, which is filtered off and dried under a strong vacuum for 2 days. 206 mg of product are obtained in the form of an orange powder.

LC/MS/UV: MH+306 (94.3%)

$^1$H NMR (500 MHz, DMSO-D6) δ (ppm): 7.74 (s, 1H), 7.77 (d, J=8.8 Hz, 1H), 7.84 (d, J=8.8 Hz, 1H), 7.92 (d, J=5.7 Hz, 2H), 8.45 (d, J=5.0 Hz, 3H), 8.46 (s, 1H), 8.51 (s, 1H), 10.82 (s, 1H), 13.9 (s, 1H)

Example 9

Compound No. 14

N-{3-[(Ethylamino)methyl]phenyl}-5-isoquinolin-4-yl-1H-indazole-3-carboxamide dihydrochloride Intermediate 9.1

N-(3-Nitrobenzyl)ethaneamine hydrochloride

A solution of $BH_3$-THF (1M, 60 ml) is added dropwise, under argon, to a solution of N-(3-nitrobenzyl)acetamide (3.89 g, 20 mmol) in anhydrous THF (100 ml). The reaction mixture is stirred at 40° C. overnight. MeOH (40 ml) is added. The solvents are evaporated off under vacuum and the residue is heated for 4 h at 60° C. in a THF/4N HCl (80/25) mixture. After cooling, a solid separates. EtOAc (50 ml) is added while maintaining the stirring. The solid is filtered off, washed with EtOAc and diethyl ether, and then dried. 3.95 g of product are obtained in the form of a white powder.

Intermediate 9.2

(3-Aminobenzyl)ethylamine

Intermediate 9.1 (3.90 g, 18 mmol) in glacial acetic acid (100 ml) is stirred, under argon, at 110° C. for 30 min in the presence of iron (6.64 g, 118.8 mmol). After cooling, the iron salts are filtered off and washed with acetic acid (15 ml). The filtrate is diluted in water (200 ml) and is then brought to pH 9 by adding solid $K_2CO_3$ and to pH 12 by adding NaOH. The resulting suspension is extracted with $CH_2Cl_2$. The organic solution is dried and then evaporated, to give the expected product. 2.65 g of product are obtained in the form of a yellow oil.

Intermediate 9.3 tert-Butyl (3-aminobenzyl)ethylcarbamate

Intermediate 9.2 (2.60 g, 17.3 mmol) in solution in $CH_2Cl_2$ (150 ml) is reacted, under argon, with di-tert-butyl dicarbonate (3.89 g, 17.3 mmol) for 1 h 30 min. The solvent is evaporated off. The oil obtained is purified on silica gel by effecting an elution gradient from an EtOAc/$CH_2Cl_2$ (1/9) mixture to an EtOAc/$CH_2Cl_2$ (1/4) mixture. 1.28 g of product are obtained in the form of a colourless gum.

Intermediate 9.4 tert-Butyl (3-{[(5-bromo-1-(2-trimethylsilyl-ethoxymethyl)-1H-indazol-3-yl)carbonyl]amino}benzyl)ethyl-carbamate A solution of isopropyl chloroformate in toluene (1M, 5.5 ml, 5.5 mmol), and then N-methylmorpholine (600 µl, 5.5 mmol), are added, at 0° C., under argon, to a solution of 5-bromo-1-(2-trimethylsilylethoxymethyl)-1H-indazole-3-carboxylic acid (1.86 g, 5 mmol), prepared from 5-bromoisatin in a manner similar to intermediate 1.2, in anhydrous THF (45 ml). The mixture is stirred for 20 min at 0° C. and then for 15 min at ambient temperature. After cooling to 0° C., intermediate 9.3 (1.38 g, 5.5 mmol) in solution in anhydrous THF (5 ml) is added. The reaction mixture is stirred for 5 h at ambient temperature and is then concentrated under vacuum. The residue is taken up with EtOAc/$H_2O$. The organic phase is washed with 10% $K_2CO_3$, dried, and then evaporated under vacuum. 2.81 g of product are obtained in the form of a yellow gum.

Intermediate 9.5 tert-Butyl ethyl(3-{[(5-isoquinolin-4-yl-1-(2-trimethylsilylethoxymethyl)-1H-indazol-3-yl)carbonyl]-amino}benzyl)carbamate Isoquinolin-4-ylboronic acid (461 mg, 2 mmol) and then aqueous $Na_2CO_3$ solution (2M, 5 ml, 10 mmol) are added to a solution of intermediate 9.4 (1.21 g, 2 mmol) in DME (12 ml). The reaction mixture is degassed with argon and then tetrakis(triphenylphosphine)palladium (116 mg, 0.1 mmol) is added. After further degassing, the mixture is heated at 80° C. for 20 h. The reaction mixture is evaporated under vacuum and is then taken up in EtOAc/$H_2O$ and filtered. The EtOAc solution is dried and then evaporated under vacuum. The residue is purified on silica gel, elution being carried out with an EtOAc/DCM (1/3) mixture. 1.08 g of product are obtained in the form of a yellow gum.

N-{3-[(Ethylamino)methyl]phenyl}-5-isoquinolin-4-yl-1H-indazole-3-carboxamide dihydrochloride TFA (20 ml) cooled to 4° C. is added to intermediate 9.5 (1.0 g, 1.53 mmol), under argon. The mixture is stirred for 2 h at ambient temperature. The TFA is evaporated off under vacuum. The residue is taken up with toluene and the mixture is then evaporated under vacuum. This process is repeated. The residue is taken up in THF (50 ml). Ethylenediamine (620 µl, 9.20 mmol) is added and the mixture is heated at 70° C. under argon overnight. The mixture is evaporated and the residue is extracted with EtOAc/H$_2$O. The organic phase, after drying and evaporation, gives a compound which is solubilized in an isopropanol/4N HCl (20 ml/2 ml) mixture. The solid that slowly separates is filtered off. 622 mg of product are obtained in the form of a yellow solid.

LC/MS/UV: MH+422 (100%)

$^1$H NMR (500 MHz, DMSO-D6) δ (ppm): 1.21 (t, J=6.9 Hz, 3H), 2.95 (m, 2H), 4.09 (t, J6.0 Hz, 2H), 7.30 (d, J=7.6 Hz, 1H), 7.40 (t, J=7.9 Hz, 1H), 7.68 (d, J=10.1 Hz, 1H), 7.81 (d, J=8.2 Hz, 1H), 7.92 (d, J=8.2 Hz, 1H), 7.97 (t, J=7.9 Hz, 1H), 8.07 (m, 1H), 8.12 (s, 1H), 8.12 (s, 1H), 8.41 (s, 1H), 8.53 (d, J=7.6 Hz, 1H), 8.67 (s, 1 H), 9.1 (broad s, 2H), 9.78 (s, 1H), 10.55 (s, 1H), 14.2 (s, 1H).

The table which follows illustrates the chemical structures and the physical properties of some compounds that can be used in accordance with the present invention. In this table:

- in the "salt" column, "-" represents a compound in the form of a free base, whereas "HCl" represents a compound in the form of a hydrochloride. The ratio in brackets is the acid/base ratio;
- Mp (° C.) represents the melting point of the compound, in degrees Celsius; and
- M+H represents the mass of the compound plus 1.

TABLE

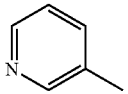

(I)

| No. | R$_1$ | n | Ar | Salt | M+H | Mp (° C.) |
|---|---|---|---|---|---|---|
| 1 | 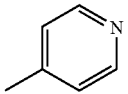 | 0 | 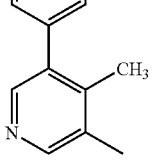 | HCl (1/1) | 316 | 196 |
| 2 | 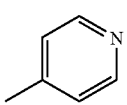 | 0 | 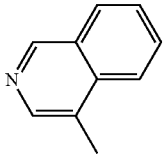 | HCl (1/1) | 407 | 192 |
| 3 | 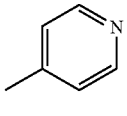 | 0 | 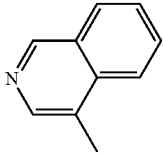 | — | 366 | >250 |
| 4 | 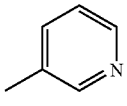 | 1 | 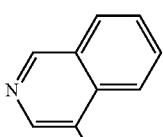 | — | 380 | 238 |
| 5 | 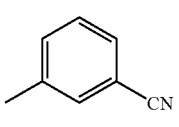 | 0 |  | — | 390 | >260 |

TABLE-continued (I)

| No. | R₁ | n | Ar | Salt | M + H | Mp (° C.) |
|---|---|---|---|---|---|---|
| 6 | 4,5-dimethyl-3-pyridyl (with pyridine attached) | 0 | 4-methylpyridyl | — | 407 | >250 |
| 7 | 2H-tetrazol-5-yl | 0 | 4-methylpyridyl | HCl (1/1) | 307 | >250 |
| 8 | 3-pyridyl | 0 | 4-(NHSO₂CH₃)phenyl | HCl (1/1) | 408 | >250 |
| 9 | 5-methylthiazolyl | 0 | 4-methylpyridyl | — | 322 | >250 |
| 10 | 4-methyl-pyrrolo[2,3-c]pyridine | 0 | 4-methylpyridyl | — | 355 | >250 |
| 11 | 4-methylpyrazolyl | 0 | 4-methylpyridyl | — | 305 | — |
| 12 | 6-chloro-3-methylpyridyl | 0 | 4-methylpyridyl | — | 350 | >250 |
| 13 | 5-methyloxazolyl | 0 | 4-methylpyridyl | — | 306 | >250 |
| 14 | 4-methylisoquinolinyl | 0 | 3-(NHCH₂CH₃)phenyl | HCl (2/1) | 422 | >135 |

TABLE-continued (I) structure: R₁-substituted 1H-indazole-3-carboxamide with N-H-(CH₂)nAr

| No. | R₁ | n | Ar | Salt | M+H | Mp (°C.) |
|---|---|---|---|---|---|---|
| 15 | 3-amino-4,5-dimethylpyridin-... (H₂N, CH₃ on pyridine) | 0 | 4-methylpyridin-... | — | 345 | — |
| 16 | 4-methyl-N-(2-amino-2-oxoethyl)nicotinamido- | 0 | 4-methylpyridin-... | — | 430 | — |
| 17 | 3-methylpyridin- | 0 | 4-(SO₂NH₂)phenyl- (para) | — | 394 | — |
| 18 | 3-methylpyridin- | 0 | 3-(SO₂NH₂)phenyl- (meta) | — | 394 | — |
| 19 | 3-methylpyridin- | 0 | 4-(S(O)₂-NH-pyrimidin-2-yl)phenyl- | — | 472 | >260 |
| 20 | 3-methylpyridin- | 1 | 4-(SO₂NH₂)phenyl- | — | 407 | >260 |
| 21 | 4-methyl-1H-pyrrolo[3,2-c]pyridin- | 0 | 3-((ethylamino)methyl)phenyl- | — | 411 | >250 |

The compounds of formula (I) were the subject of in vitro pharmacological assays, which showed their inhibitory activity on *P. falciparum*.

Two strains of *P. falciparum* are used, the origin of which is Colombia (FcB1, strain moderately resistant to chloroquine) and Cameroon (FcM29, strain highly resistant to chloroquine). These strains of *P. falciparum* are cultured continuously in human red blood cells according to the method of Trager and Jensen (W. Trager, J. Jensen, Science, 1976, 193, 673-675): the parasites are maintained in human red blood cells (O±), diluted to 2% parasiteamia in an RPMI 1640 medium supplemented with 25 mM of Hepes, 24 mM of NaHCO$_3$ and 2 mM of L-glutamine, and supplemented with 5% of human serum of all groups. The parasites are incubated at 37° C. in a humid atmosphere and at 5% CO$_2$.

The antimalarial activity assays are carried out according to the radioactive micromethod of Desjardins (R. E. Desjardins, C. J. Canfield, J. D. Haynes, J. D. Chulay, Antimicrob. Agents Chemother., 1979, 16, 710-718). Each molecule is tested in triplicate. The assays are carried out in 96-well microplates. The strains of *P. falciparum* are cultured in solutions of RPMI 1640 supplemented with 5% of human serum with a 2% haematocrit and a 1.5% parasitaemia. For each assay, the parasites are incubated with decreasing concentrations of compounds of formula (I) for 48 h at 37° C. in a humid atmosphere and at 5% $CO_2$.

The first dilution of the test compound is prepared at 1 mg/ml in dimethyl sulphoxide. The dilution range for the successive daughter solutions is also prepared in dimethyl sulphoxide. Each daughter dilution is subsequently diluted to 1/50 in RPMI 1640 supplemented with 5% of human serum, all the dilutions being prepared at 37° C. These dilutions are then added to the parasites in culture in the microplates. After addition of the test compound, the parasites are in culture in RPMI 1640 containing 5% of human serum and 1% of dimethyl sulphoxide. The parasite growth is measured by the incorporation of tritiated hypoxanthine (added 24 h after the beginning of exposure to the test compound) compared with incorporation in the absence of the test compound (taken as 100%). The $IC_{50}$ values (concentration of the compound required to inhibit the parasite growth by 50%) are determined by plotting the percentage inhibition as a function of the log of the dose by means of the GraphPad Prism 4® processing software (GraphPad software, Inc., 5755 Oberlin Drive, # 110, San Diego, Calif. 92121, USA).

The $IC_{50}$ values measured for the compounds of formula (I) on one or other of the *P. falciparum* strains used are, for the most active compounds, less than 1 µM. For example, compound Nos. 3, 10, 11, 12, 14 and 21 in the above table exhibit, respectively, $IC_{50}$ values of 600, 130, 800, 800, 272 and 406 nM on the strain FcM29.

The results of these assays show that the compounds of formula (I) and their pharmaceutically acceptable salts can be used for preparing medicinal products intended for the treatment and prevention of malaria.

To this effect, the compounds of formula (I) and their salts can be provided in any of the pharmaceutical forms suitable for oral, sublingual, injectable (such as subcutaneous, intramuscular and intravenous), topical, local, intratracheal, intranasal, transdermal or rectal administration, in combination with suitable excipients.

The present invention, according to another of its aspects, also concerns a method for treating and/or preventing malaria, which comprises the administration, to a patient, of an effective dose of a compound of formula (I), or one of its pharmaceutically acceptable salts or hydrates or solvates.

What is claimed is:

1. A method of treating malaria or inhibiting *Plasmodium falciparum* parasite in a patient in need thereof, which comprises administering to said patient an effective amount of a compound corresponding to general formula (I):

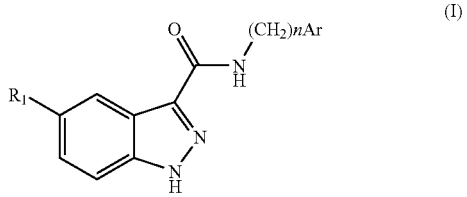

in which:
$R_1$ represents a heteroaromatic group optionally substituted with one or two substituents chosen, independently of one another, from halogen atoms and heteroaromatic, $C_{1-6}$ alkyl, —OH, —$NH_2$, —$NHR_2$, —$NHCOR_2$, —$COOR_2$, —$CONH_2$, —$CONHR_2$ and —$CH_2XR_2$ groups, where X is chosen from O, NH and S;

Ar represents a heteroaromatic group optionally substituted with one or two substituents chosen, independently of one another, from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups;

$R_2$ and $R_3$, which may be identical to or different from one another, represent a $C_{1-6}$ alkyl group optionally substituted with a —$CONH_2$ group, with a phenyl group or with a heteroaromatic group;

or else $R_2$ and $R_3$, which may be identical to or different from one another, represent a phenyl group or a heteroaromatic group; and n is equal to 0, 1, 2 or 3, or a pharmaceutically acceptable salt, hydrate or solvate thereof.

2. The method according to claim 1, wherein the compound of general formula (I) is such that:
$R_1$ represents a heteroaromatic group optionally substituted with one or two substituents chosen, independently of one another, from halogen atoms and heteroaromatic, $C_{1-6}$ alkyl, —$NH_2$ and —$CONHR_2$ groups.

3. The method according to claim 1, wherein the compound of general formula (I) is such that:
$R_2$ and $R_3$, which may be identical to or different from one another, represent a $C_{1-6}$ alkyl group optionally substituted with a —$CONH_2$ group; or else $R_2$ and $R_3$, which may be identical to or different from one another, represent a phenyl group or a heteroaromatic group.

4. The method according to claim 1, wherein the compound of general formula (I) is such that:
n is equal to 0 or 1.

5. The method according to claim 1, wherein $R_1$ represents a pyrazolyl, thiazolyl, tetrazolyl, oxazolyl, pyridinyl, isoquinolinyl or pyrrolo[2,3-c]pyridinyl group.

6. The method according to claim 1, wherein
Ar represents a pyridinyl group optionally substituted with one or two substituents chosen, independently of one another, from halogen atoms and $C_{1-6}$ alkyl, $C_{1-6}$ thioalkyl, $C_{1-6}$ alkoxy, —$CH_2OH$, phenoxy, morpholinyl, —$CH_2$-morpholinyl, —$NH_2$, —$NHR_2$, —$NR_2R_3$, —$NHSO_2R_2$, —CN, —$SO_2R_2$, —$SO_2NH_2$, —$SO_2NHR_2$, —COOH, —$COOR_2$, —$CONH_2$, —$CONHNH_2$, —$CONHR_2$, —$CH_2NHR_2$ and —$CH_2NR_2R_3$ groups.

7. The method according to claim 1, wherein $R_2$ and $R_3$, which may be identical to or different from one another, represent a methyl or ethyl group optionally substituted with a —$CONH_2$ group; or else $R_2$ and $R_3$, which may be identical to or different from one another, represent a phenyl group or a heteroaromatic group.

8. The method according to claim 1, wherein the compound of general formula (I) is chosen from:
N-(pyridin-4-yl)-5-isoquinolin-4-yl-1H-indazole-3-carboxamide,
N-(pyridin-4-yl)-5-(1H-pyrrolo[2,3-c]pyridin-4-yl)-1H-indazole-3-carboxamide,
5-(1H-pyrazol-4-yl)-N-(pyridin-4-yl)-1H-indazole-3-carboxamide,
5-(6-chloropyridin-3-yl)-N-pyridin-4-yl-1H-indazole-3-carboxamide,
N-{3-[(ethylamino)methyl]phenyl}-5-isoquinolin-4-yl-1H-indazole-3-carboxamide, and
N-{3-[(ethylamino)methyl]phenyl}-5-(1H-pyrrolo[2,3-c]pyridin-4-yl)-1H-indazole-3-carboxamide,
or a pharmaceutically acceptable salt, hydrate or solvate thereof.

* * * * *

UNITED STATES PATENT AND TRADEMARK OFFICE
CERTIFICATE OF CORRECTION

| | | |
|---|---|---|
| PATENT NO. | : 7,842,711 B2 | Page 1 of 2 |
| APPLICATION NO. | : 11/531332 | |
| DATED | : November 30, 2010 | |
| INVENTOR(S) | : Hugues D'Orchymont et al. | |

It is certified that error appears in the above-identified patent and that said Letters Patent is hereby corrected as shown below:

In column 10, in Structures, line 4-33, delete

" 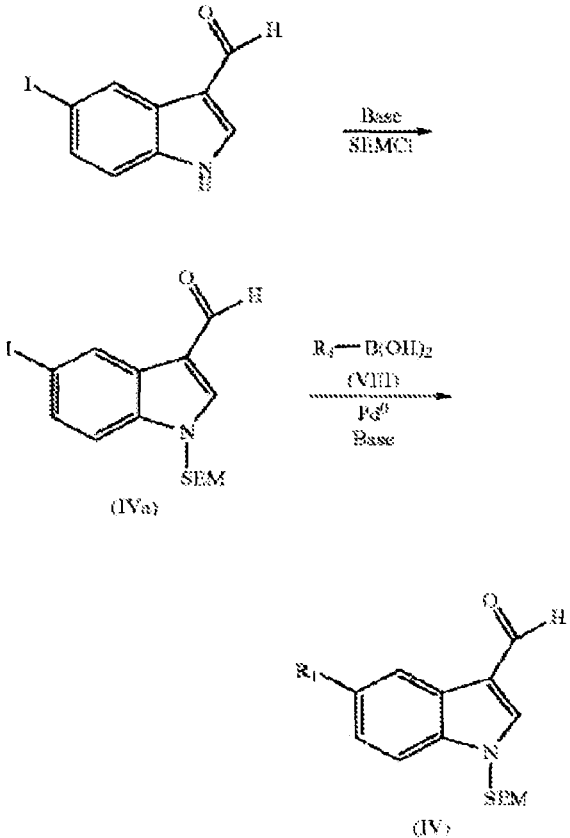 "

Signed and Sealed this
Twenty-third Day of August, 2011

David J. Kappos
*Director of the United States Patent and Trademark Office*

CERTIFICATE OF CORRECTION (continued)
U.S. Pat. No. 7,842,711 B2 and insert

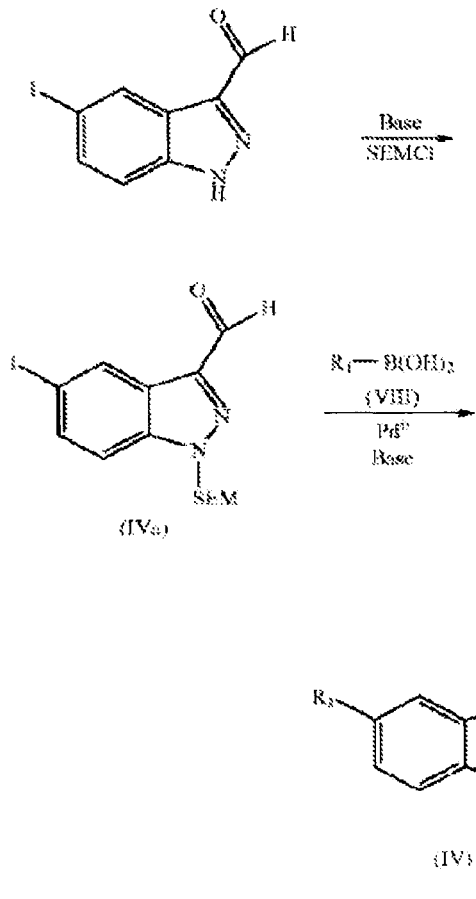

-- --, therefor.